United States Patent [19]
Grimard et al.

[11] Patent Number: 5,607,399
[45] Date of Patent: Mar. 4, 1997

[54] BACKSTOP DEVICE FOR A FLANGELESS SYRINGE

[75] Inventors: Jean P. Grimard, Vif; Eric Olive, Lyons, both of France

[73] Assignee: Becton, Dickinson and Company, Franklin Lakes, N.J.

[21] Appl. No.: 532,444

[22] Filed: Sep. 22, 1995

[51] Int. Cl.[6] ............................................. A61M 5/315
[52] U.S. Cl. ............................................. 604/220
[58] Field of Search .................................. 604/220, 187, 604/110, 218, 232, 227

[56] References Cited

U.S. PATENT DOCUMENTS

| | | | |
|---|---|---|---|
| 4,711,637 | 12/1987 | Leigh et al. | 604/220 |
| 4,883,471 | 11/1989 | Braginetz et al. | 604/195 |
| 4,946,441 | 8/1990 | Laderoute | 604/110 |
| 5,019,053 | 5/1991 | Hoffman et al. | 604/220 |
| 5,358,497 | 10/1994 | Dorsey et al. | 604/220 |

FOREIGN PATENT DOCUMENTS

| | | |
|---|---|---|
| 0409134A1 | 1/1991 | European Pat. Off. . |
| 2945869A2 | 5/1981 | Germany . |
| WO94/26334 | 11/1994 | WIPO . |

*Primary Examiner*—John D. Yasko
*Attorney, Agent, or Firm*—Vincent A. Castiglione

[57] ABSTRACT

A backstop device to prevent inadvertent withdrawal of a stopper or plunger rod from the open distal end of a flangeless syringe barrel. The backstop includes a retaining wall configured to engage at least a portion of the syringe barrel, and a finger plate at the proximal end of the retaining wall. The finger plate includes an aperture adjacent the open proximal end of the syringe through which a stopper may be inserted. If desired, a ridge may be formed around the periphery of the aperture which may engage with a portion of the syringe barrel. The aperture and, if present, the ridge present a smaller passageway than the inside diameter of the syringe, preventing inadvertent removal of the stopper from the syringe. The backstop can be placed on the syringe regardless of the presence or absence of the plunger.

9 Claims, 11 Drawing Sheets

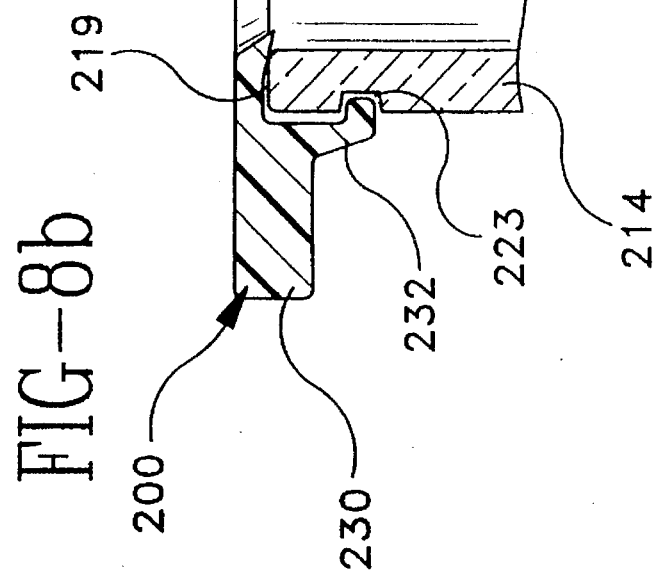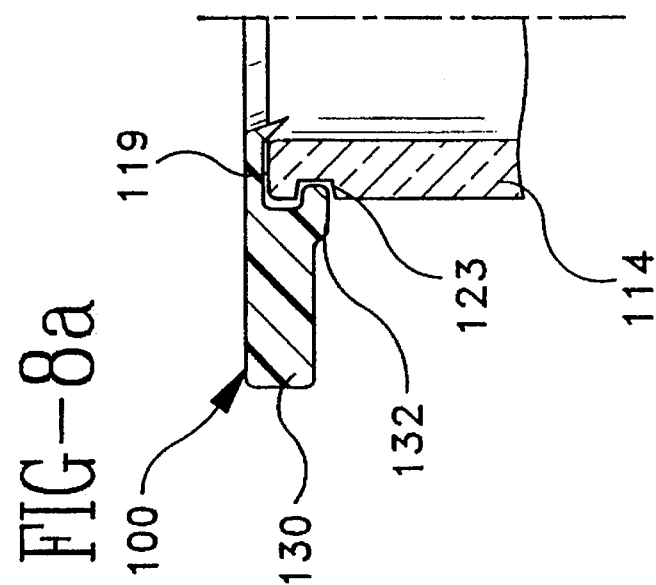

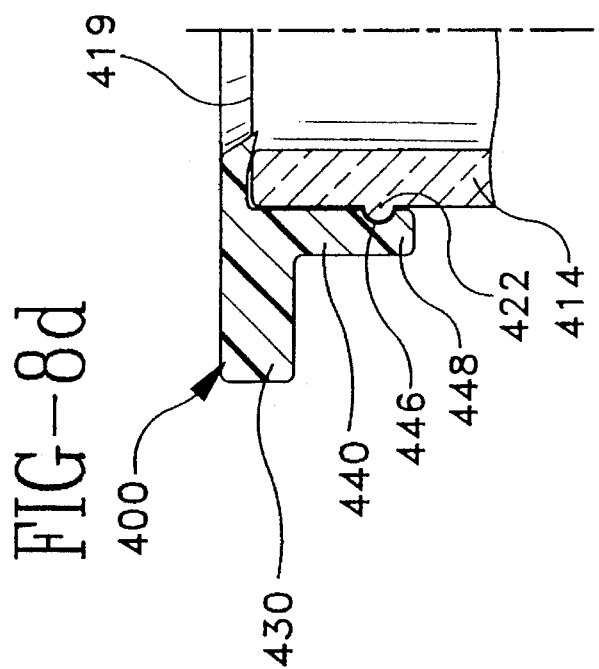
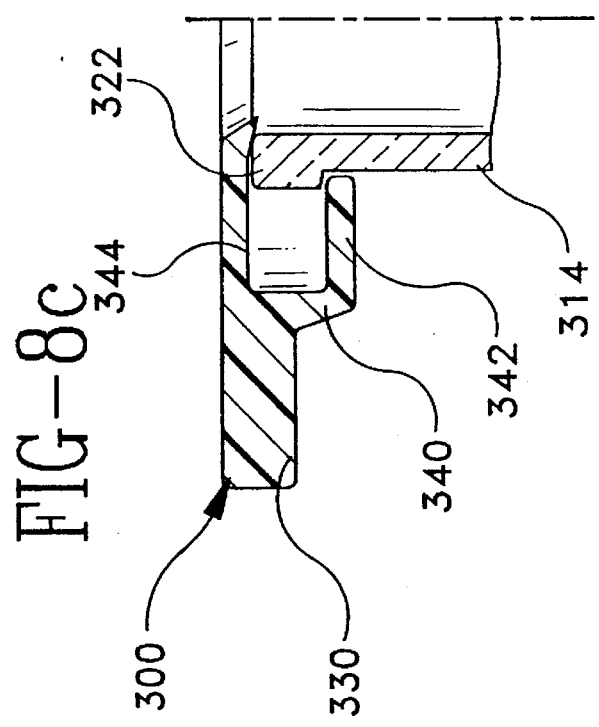
FIG-8d
FIG-8c

BACKSTOP DEVICE FOR A FLANGELESS SYRINGE

I. FIELD OF THE INVENTION

The invention relates to a backstop device for a syringe, and more particularly, to a backstop device for a flangeless syringe which prevents inadvertent removal of the stopper component associated with the syringe.

II. BACKGROUND

As is known in the art, syringes are medical delivery devices utilizable to administer a medicament to a patient. Syringes are normally marketed either in prefilled form, wherein a set dosage of medicament is already provided therein, or they are empty and intended to be filled from a vial or other source of medicament by an end user at the time administration of the medicament is desired.

Syringes typically include a barrel portion adapted to retain the medicament. The distal end of the barrel is normally configured to mate with a conventional piercing element, such as a pointed needle cannula made of steel or like material or a blunt ended cannula formed of plastic, to deliver the medicament contained in the barrel. A plunger rod is inserted through the open distal end of the syringe barrel and, through its engagement with an elastomeric or rubber-like stopper element fitted in a fluid-tight manner within the interior of the barrel, a user can apply manual force to the plunger to deliver the medicament through the piercing element. A flange is sometimes provided around the open distal end of the syringe barrel as a form of finger rest to facilitate a user's manipulation of the device. However, some syringes, often referred to as "flangeless" syringes, do not feature a flange.

As the skilled artisan will appreciate, one problem with either pre-filled syringes or empty syringes is that the stopper element can be inadvertently dislodged from the syringe barrel, rendering the syringe itself unusable and/or the medicament therein unsterile. For instance, particularly in the case of pre-filled syringes, forces exerted on the stopper during terminal sterilization procedures could cause the stopper to eject from the open distal end of the syringe, rendering the product unusable. Also, end users attempting to aspirate medicament through the piercing element into the syringe barrel could, inadvertently, exert excess force onto the plunger, causing the stopper and/or the plunger rod affixed to the stopper to dislodge from the barrel. There is also the risk that for certain medicaments, such as cytotoxic drugs, safety concerns dictate that the stopper not be dislodged from the barrel.

Numerous attempts in the art have sought to address the aforementioned concerns. For instance, U.S. Pat. No. 4,711,637 to Leigh et al. describes a syringe lock formed as a clip made from a malleable material such as sheet metal. The clip, affixed to the proximal end of the syringe, includes a protrusion jutting towards the interior portion of the barrel which serves to "bite" into the plunger so as to arrest movement thereof once a desired plunger position is achieved. In this type of device, inadvertent rotation of the plunger could cause unwanted locking, rendering the syringe unusable. Another clip-type approach is found in U.S. Pat. No. 4,883,471 to Braginetz et al., wherein a spring clip is disposed around the exterior of the syringe barrel. The clip includes finger elements protruding through apertures formed in the syringe barrel. The finger elements physically arrest the stopper element once a desired plunger extension is reached.

Alternately, structure may be incorporated as part of the syringe barrel itself to physically restrain the syringe stopper from inadvertent withdrawal. Examples of these approaches are found, inter alia, in U.S. Pat. No. 4,946,441 to Laderoute and European Patent Application No. 0 409 134 to Escudero. These approaches are oftentimes uneconomical in that costly modifications will be required to molding equipment to achieve the desired structure. In addition, by employing specific, integral syringe barrel construction, the user is deprived of the ability to effect easy, intentional removal of the stopper by disabling the stopper lock structure, if such action is desired.

PCT Application WO 94/26334 discloses, inter alia, two embodiments of a plunger lock device for a syringe. A first embodiment is of the spring clip type and includes a finger portion 61 jutting into the interior of the syringe barrel. The finger portion 61 physically arrests the stopper from inadvertent withdrawal. A second embodiment entails a disk-like addition which mounts to the flange area of the syringe. The top portion of the disk includes an aperture, aligned with the syringe barrel, that is smaller than the internal diameter of the barrel. While the smaller diameter disk aperture prevents the stopper from inadvertent withdrawal, this embodiment can only be effected where the disk is first mounted to the syringe flange and the plunger thereafter inserted through the disk aperture for attachment to the stopper. Accordingly, the disk device as taught therein is mainly intended for use where it is shipped intact with a fully assembled syringe, and most likely where affixation of the plunger lock device is part of the syringe filling, assembly and/or sterilization processes. Most syringe processing machinery, however, is not set up to accommodate manipulation of the lock device, and modifications to the production line can be costly if not difficult.

For reasons of economy, and particularly where specialized filling or sterilization machinery is already in place, it would be advantageous to ship the stopper lock device apart from a pre-filled or pre-assembled syringe for later affixation. It would also be advantageous to permit affixation of the device as an add-on component, without having to disrupt the plunger from the stopper or to otherwise modify the existent production line. In addition, it would be advantageous to accommodate such a device to a flangeless syringe, both to deter the stopper from inadvertent withdrawal and to provide the user with a finger rest to manipulate the syringe.

III. SUMMARY OF THE INVENTION

These and related concerns are addressed by a syringe backstop device in accordance with the present invention. The device, readily applicable to either plastic or glass syringes, may be formed as a plate-like structure, and may be adapted to the dimensions of a flangeless syringe in a manner to enhance a user's grip of the device. In addition to performing a backstop function, the device may be employed to provide a flange for an otherwise flangeless syringe.

In one embodiment, the backstop features a retaining wall affixable about the outer circumference of a syringe barrel. For instance, the retaining wall may be configured as a circumferential wall formed so as to engage at least a portion of the circumference of the syringe barrel, and placeable on the syringe barrel in a direction lateral to the longitudinal axis of the syringe barrel. The circumferential wall may display an opening having a width approximately as wide as the outside diameter of the syringe barrel in order to facilitate placement of the backstop onto the syringe barrel. If desired, the opening can be made slightly narrower than the diameter of the syringe barrel to facilitate a snap-fit type, locking retention of the retaining wall to the syringe barrel. The retaining wall may include various protrusions or recesses adapted to mate with corresponding grooves or shoulders provided on the syringe barrel.

The backstop further features a finger plate affixed to the proximal end of the retaining wall. The finger plate may be configured with a flange-like shape to enable a user to more readily manipulate the syringe, while at the same time providing structure for averting unwanted removal of the stopper from the syringe barrel. The finger plate includes an aperture aligned with the open proximal end of the syringe barrel adapted to prevent inadvertent withdrawal of the stopper, and/or the plunger rod, from the syringe barrel. In one configuration, the top aperture is formed through the finger plate with a frusto-conically-shaped sloping wall. The diameter of the aperture at the terminus of the sloping wall measures less than the inside diameter of the syringe barrel. The difference in these diameters establishes an aperture overhang preventing the inadvertent withdrawal of the stopper or plunger rod from the syringe barrel.

In lieu of the aperture overhang or supplemental to it, a ridge element may be disposed about the periphery of the aperture to prevent inadvertent withdrawal of the stopper from the syringe barrel. The aperture permits insertion of the stopper or plunger rod even after the backstop is in place, while the ridge prevents inadvertent withdrawal of the stopper or plunger rod from the syringe barrel.

The finger plate may also feature an opening between the aperture and the perimeter of the plate wide enough to accommodate entry of a plunger rod into the aperture. The finger plate opening is preferably aligned with the opening of the retaining wall. Accordingly, the backstop may be mounted to the syringe barrel in a lateral direction regardless of the presence or absence of the plunger rod.

In lieu of providing a finger plate with aperture at the proximal end of the retaining wall, a pair of flange rests might be affixed to the retaining wall, thereby creating an add-on flange for a flangeless syringe. Also, the aperture of the backstop might be deleted, either by forming the finger plate without an aperture or by employing various sealing means, providing a handy closure device for a syringe barrel.

IV. BRIEF DESCRIPTION OF THE DRAWINGS

The invention will now be described in greater detail by way of reference to the appended drawings, wherein:

FIGS. 8a–8d illustrate various means for adapting the backstop of the present invention to various flangeless syringes.

V. DETAILED DESCRIPTION OF THE INVENTION

A convention utilized throughout this description is that the term "distal" refers to the direction furthest from a practitioner, while the term "proximal" refers to the direction closest to a practitioner.

Figure 1:
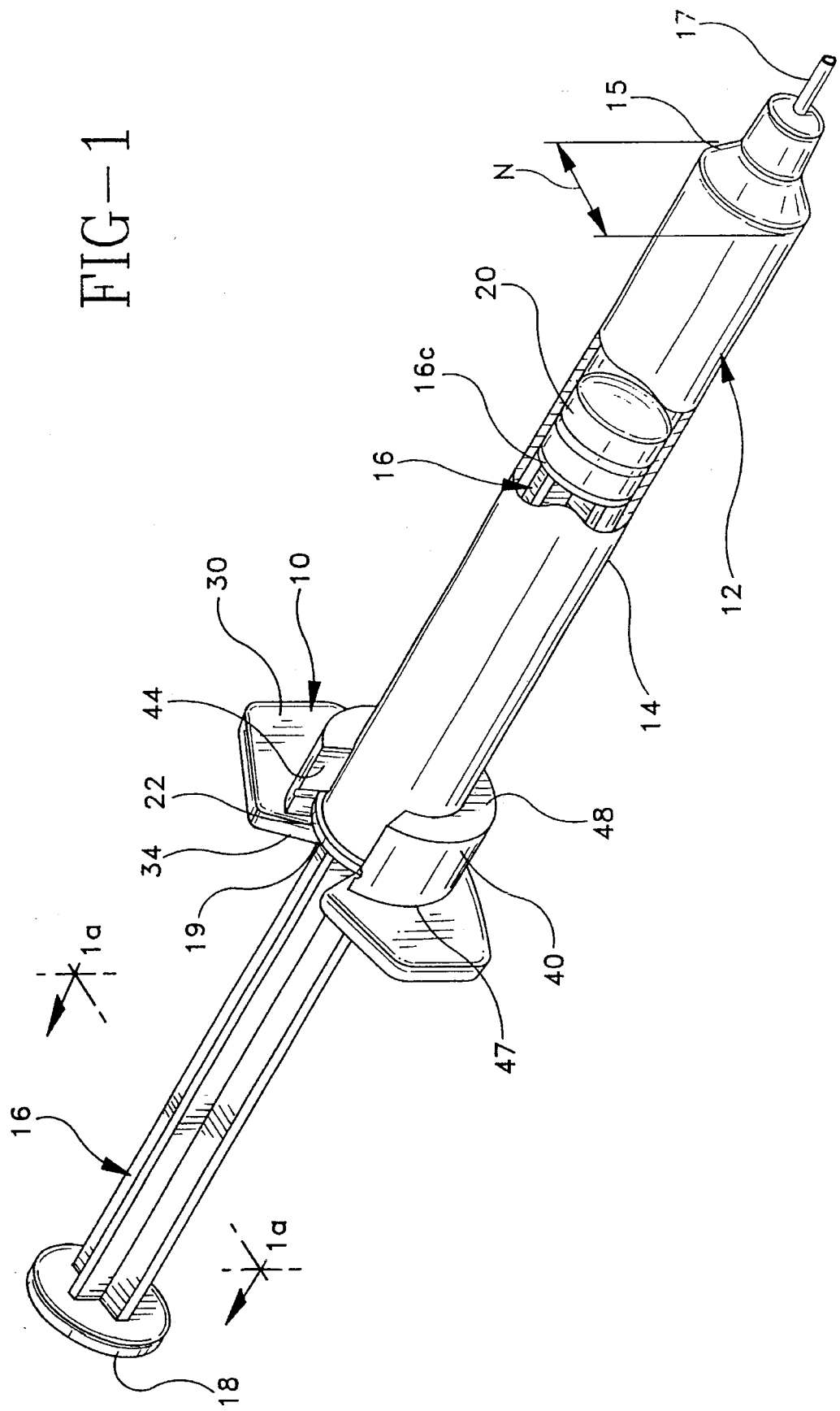
FIG. 1 depicts of the backstop device of the present invention mounted to a syringe.
Figure 2:
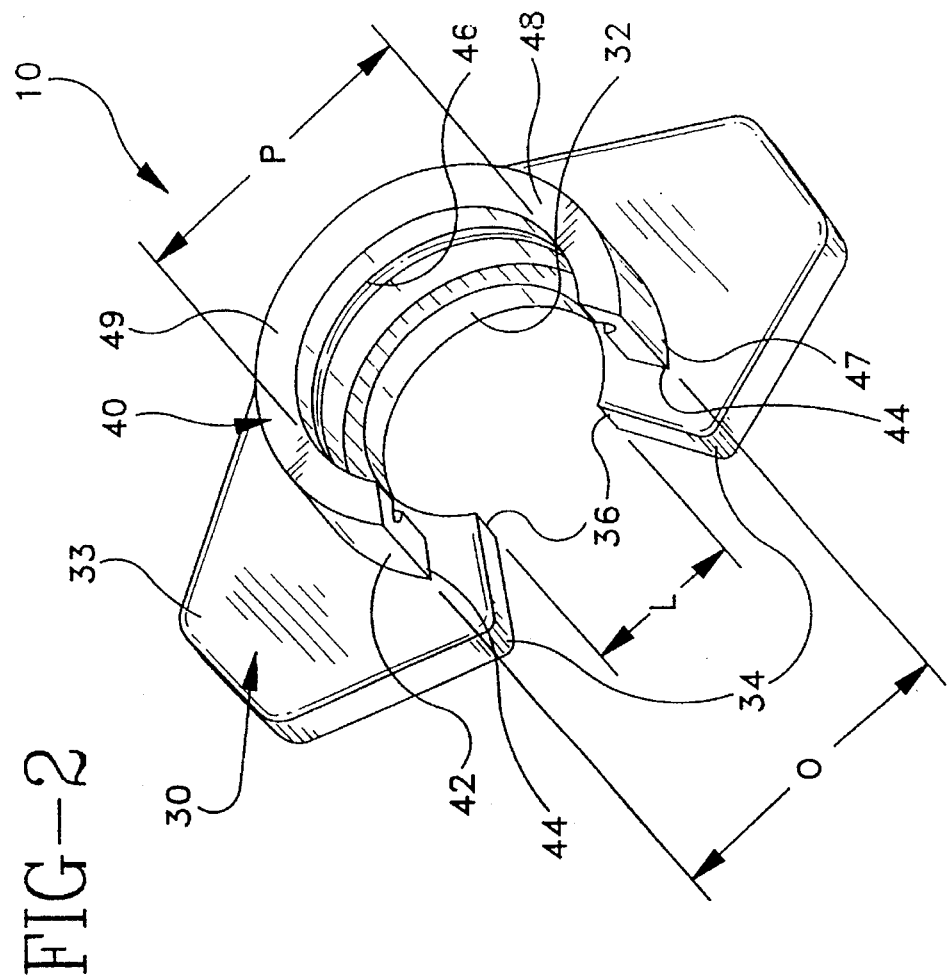
FIG. 2 depicts, in bottom perspective view, one embodiment of a backstop device in accordance with the present invention.
Figure 3A:
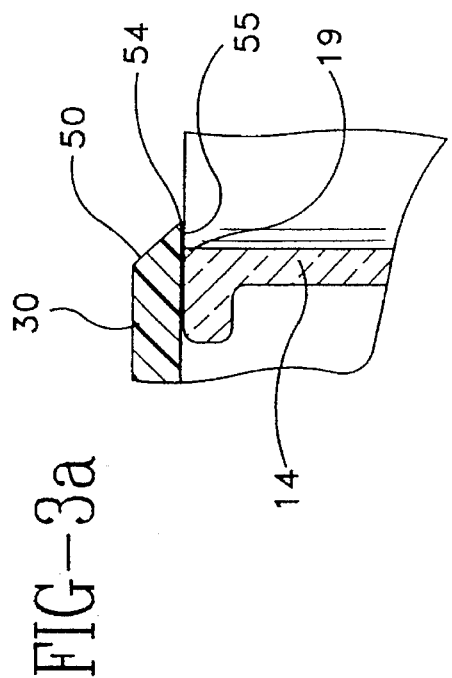
FIG. 3a illustrates placement of the finger plate aperture relative to the open proximal end of the syringe barrel.
Figure 4:
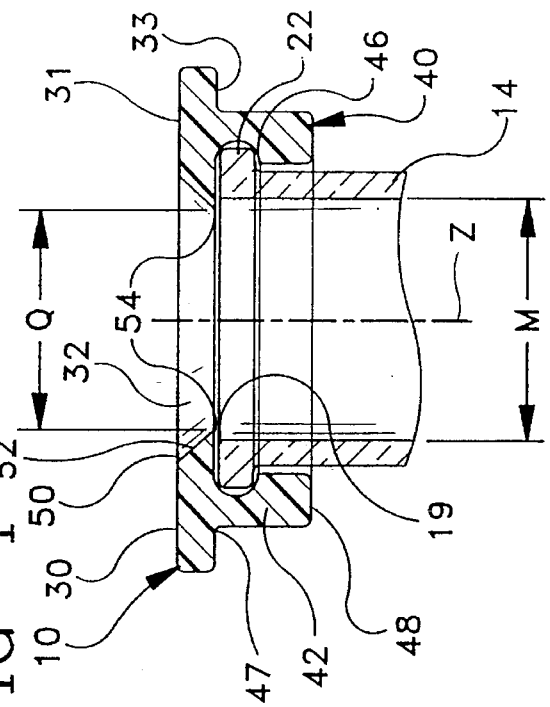
FIG. 4 is a cut-away view of the embodiment depicted in FIG. 2, as seen along line 4—4 of FIG. 3.
Figure 3:
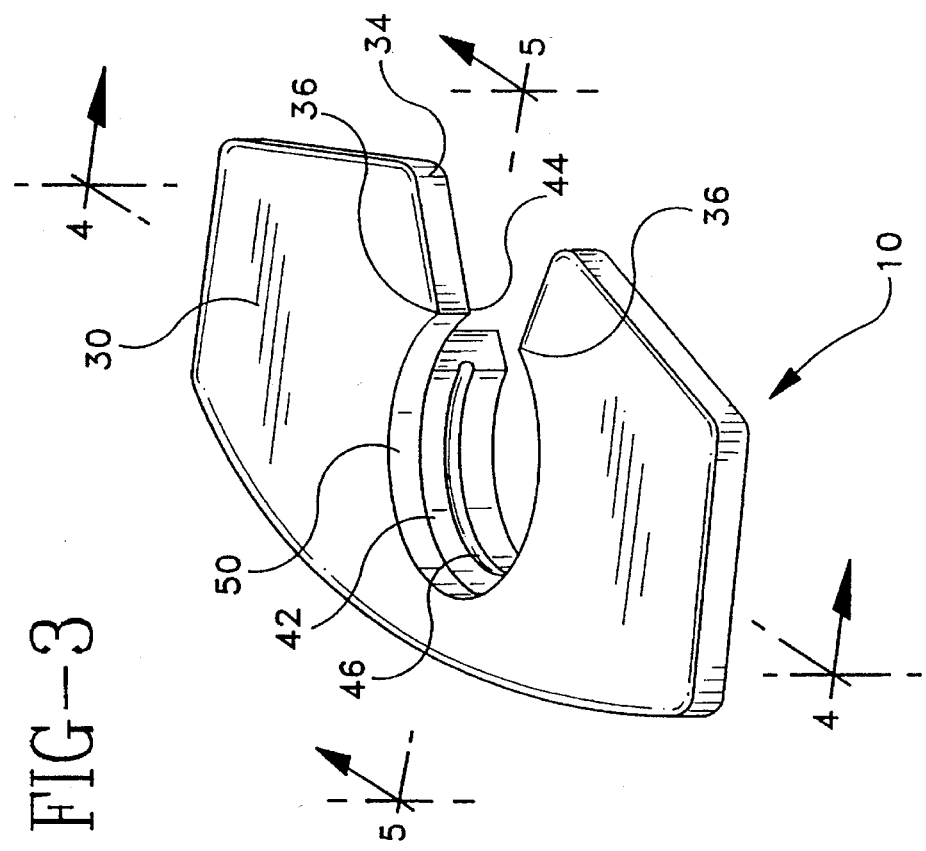
FIG. 3 is a top view of the backstop device of FIG. 2.

Turning now to the drawings, wherein like numerals denote like components, FIGS. 2–4 depict one embodiment of a backstop 10 in accordance with the present invention. FIG. 1 illustrates the backstop 10 in perspective as mounted to a medical delivery device such as a syringe 12. As depicted, syringe 12 generally includes a syringe barrel 14 adapted to contain a medicament therein. Syringe barrel 14 defines an outside diameter "N", an inside diameter "M", and a longitudinal axis "Z". Syringe barrel 14 features a distal end 15 adapted in a conventional manner for attachment or mating with a piercing element 17 as previously described. For instance, distal end 15 could be formed as a male luer connector. A relatively open proximal end 19 is formed at the opposing end of syringe barrel 14, through which a rod plunger 16 is inserted. Here, syringe 12 is of the flangeless type, and typically includes a rim element 22 formed adjacent open proximal end 19 of the syringe barrel. Rim element 22 may be created for instance, during formation of the syringe barrel.

Figure 1A:
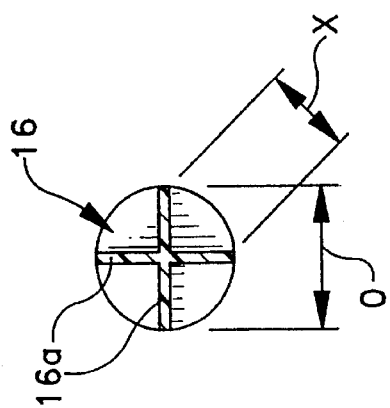
FIG. 1a depicts a cross-section of the plunger rod as seen along lines 1a—1a of FIG. 1.
Figure 1B:
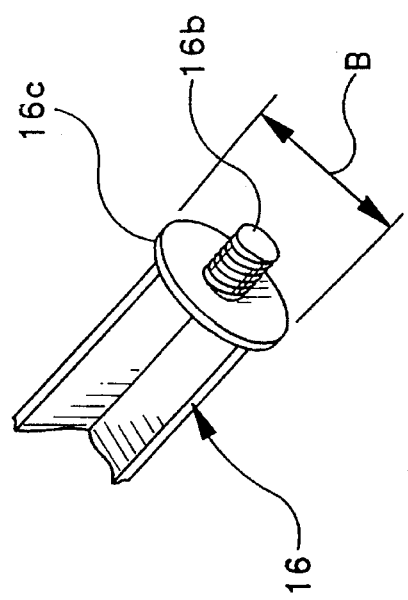
FIG. 1b is a partial cut-away view of the distal end of a plunger rod employable with the syringe.

As seen in FIG. 1a, plunger rod 16 is normally formed from a plurality of vanes 16a, defining a minimum width "x" and a maximum width "+e,sez O+ee ". Plunger rod 16 mates with a stopper element 20 disposed in fluid-tight engagement with the interior of syringe barrel 14; that is, stopper 20 defines a width at least equal to inside diameter "M" of syringe barrel 14. Plunger rod 16, which generally is provided separate from stopper 20, may mate with stopper 20 via a screw-type arrangement 16b (see FIG. 1b), or any other arrangement as the skilled artisan will appreciate. Plunger rod 16 typically includes a finger rest 18 provided at its proximal end for manipulation by a user. Also, some plunger rods may feature one or more stiffening plates 16c disposed along the length of the plunger rod. As here shown, a stiffening plate 16c is located at the distal end of the plunger rod, substantially adjacent screw-type arrangement 16b. Stiffening plate 16c defines a diameter "B" less than inside diameter "M" of syringe barrel 14, but greater than maximum diameter "+e,sez O+ee " of the plunger rod.

Turning now more particularly to FIGS. 2–4, backstop 10 in accordance with the invention features a retaining wall 40 affixable about the outer circumference of syringe barrel 14, and a finger plate 30 disposed at proximal end 47 of retaining wall 40. Finger plate 30 is affixed to retaining wall 40 in such a manner that the finger plate will rest adjacent open proximal end 19 of syringe barrel 14 when backstop 10 is fitted to the syringe. Backstop 10 may be formed from any suitable material such as medical grade plastics, metals, glass, or the like.

Finger plate 30 may be shaped in any appropriate manner enabling easy grasp by a practitioner. Here, the finger plate has been shaped to mimic a conventional syringe flange. Finger plate 30 features an aperture 32 having a width at least equal to maximum width "+e,sez O+ee " of plunger rod 16, to accommodate the insertion of the plunger rod therethrough. As will be explained in greater detail hereinbelow, aperture 32 itself and/or the structure associated therewith forms a passageway through finger plate 30 that is somewhat smaller than internal diameter "M" defined by syringe barrel 14, and is structured to prevent inadvertent withdrawal of stopper 20 or plunger rod 16 from open distal end 19 of the syringe barrel.

Finger plate 30 further includes a lead opening 34 formed or otherwise cut through the finger plate, that communicates with aperture 32 at transition points 36. Transition points 36 define the parameters demarcating aperture 32 from opening 34. Transition points 36 define a width "L" that is at least equal if not slightly greater than the minimum width "X" of plunger rod 16 such as to accommodate the insertion of plunger rod 16 into aperture 32. Thus, it will be realized that backstop 10 may be affixed to syringe barrel 14 irrespective of the presence or absence of plunger rod 16.

Retaining wall 40 is configured for snug interaction with the outside diameter "N" of syringe barrel 14. Here, retaining wall 40 includes a generally circumferential portion 42 delimited between a proximal end 47 and a distal end 46, and defining an aperture 49 with an inside diameter "P". Retaining wall 40 also includes an opening 44 having a width "O". The purpose of opening 44 is to permit backstop 10 to be slipped onto syringe barrel 14. The width "O" of opening 44 should be wide enough to enable outer diameter "N" of syringe barrel 14 to pass into inside diameter "P" of aperture 49. If desired, width "O" of opening 44 can be made slightly less than outer diameter "N" of syringe barrel 14, such that retaining wall 40, and particularly opening 44 and aperture 49, can resiliently expand about outside diameter "N" of syringe barrel 14 as it is placed thereover. Here also, inside diameter "P" of aperture 49 should be at least equal to if not slightly less than outside diameter "N" of syringe barrel 14. Thus, when the syringe barrel is fully located within aperture 49 of the retaining wall, retaining wall 40 will exert a positive holding action onto syringe barrel 14, thereby providing a type of snap-fit between the retaining wall and the syringe barrel.

As previously described, flangeless syringes may include a rim element 22 formed adjacent open proximal end 19 of the syringe barrel. Here, retaining wall 40 is provided with a groove 46 configured or otherwise formed to mate with rim element 22. Groove 46 can thus clamp about rim element 22 once retaining wall 40 is located on the syringe barrel, further supplying a positive holding force between backstop 10 and syringe barrel 14.

The backstop of the present invention may be placed onto syringe barrel 14 in a direction lateral to longitudinal axis "Z" of the syringe barrel, irrespective of the presence or absence of plunger rod 16. Referring to FIGS. 1–3, it will be seen that lead opening 34 of the finger plate and opening 44 of the retaining wall are preferably substantially aligned with one another. Thus, when urging backstop 10 in a direction lateral to longitudinal axis "Z" of the syringe barrel, opening 44 of retaining wall 40 facilitates entry of the syringe barrel into aperture 49, at the same time that lead opening 34 of the finger plate will permit plunger rod 16 (if already present in the syringe barrel) to pass into aperture 32. Accordingly, various syringe processing machinery may be accommodated which are set up for lateral-type manufacturing without the need for costly modifications, additions, or the like, for example, which might be necessitated by urging the backstop longitudinally onto the syringe barrel.

Referring to FIGS. 3 and 3a, to facilitate insertion of stopper 20 into syringe barrel 14 when backstop 10 is already present on syringe barrel 14, aperture 32 may be formed through the width of finger plate 30 in a manner to define a frusto-conical lead wall 52 that extends about the periphery of aperture 32. Frusto-conical lead wall 52 extends between a proximal periphery 50 coplanar with a top surface 31 of finger plate 30, and a distal periphery 54 located on a bottom surface 33 of finger plate 30 substantially adjacent open proximal end 19 of the syringe barrel. Distal periphery 54 of frusto-conical lead wall 52 defines a diameter "Q" less than inside diameter "M" of syringe barrel 14, but large enough to accommodate the maximum width "+e,sez O+ee " of plunger rod 16. Hence, an overhang 55 is defined extending over open proximal end 19 of the syringe barrel. Owing to frusto-conical lead wall 52, a stopper 20 may be introduced into syringe barrel 14 irrespective of the presence (or absence) of backstop 10 on the syringe barrel. At the same time, overhang 55 presents a barrier substantially preventing inadvertent withdrawal of stopper 20 from syringe barrel 14 once same has been introduced therein. Also, where structure such as stiffening plate 16c is provided on plunger rod 16, overhang 55 can be dimensioned such as to block passage of plate 16c, preventing inadvertent withdrawal of plunger rod 16 (frusto-conical lead wall 52 facilitating entry of stiffening plate 16c into the syringe barrel when backstop 10 is already in place).

If desired, a ridge element 56 may be formed about aperture 32. Here, ridge element 56 is depicted located at distal periphery 54 of frusto-conical lead wall 52, but it will be appreciated by the skilled artisan that ridge element 56 may be provided irrespective of the presence or absence of the frusto-conical lead wall about aperture 32. As herein depicted, ridge element 56 is relatively continuous, but if need or desire dictate, ridge element 56 can be formed in discontinuous sections from a plurality of individual ridge elements. Ridge element 56 may take any number of configurations, but as depicted in FIG. 3b, ridge element 56 extends through open proximal end 19 of the syringe barrel and towards its interior.

Figure 3C:
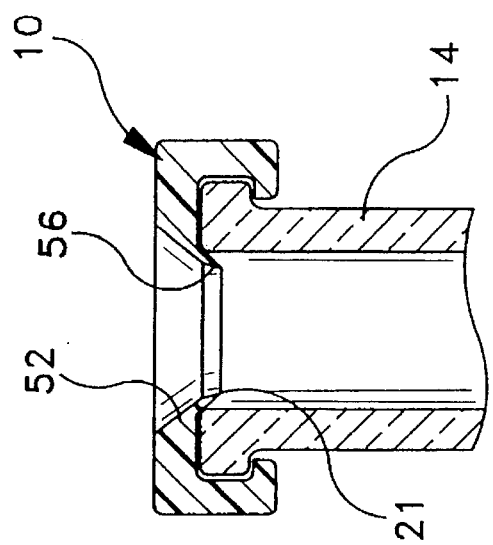
FIGS. 3b and 3c illustrate alternate formations of a ridge element around the finger plate aperture.
Figure 3B:
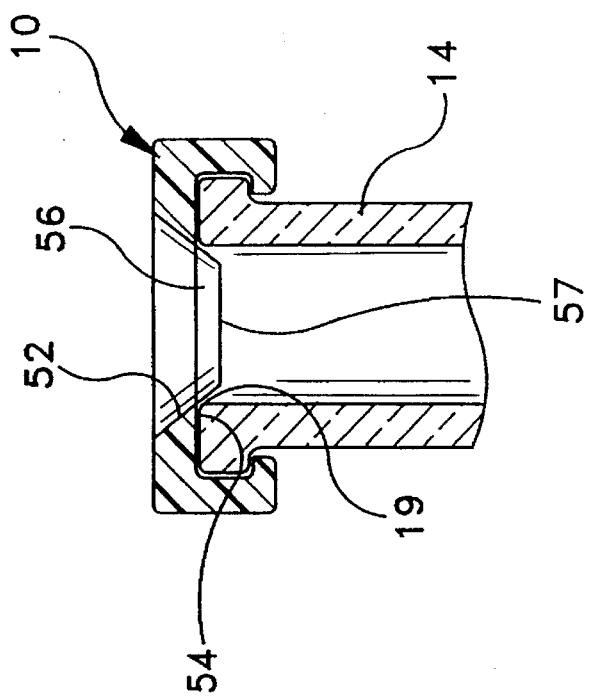

If desired, as depicted in FIG. 3c, ridge element 56 can be configured to contact a portion of syringe barrel 14, for instance, at an intersection 21 between open proximal end 19 and rim element 22 of the syringe barrel. Alternately, as previously noted respective of FIG. 3b, ridge element 56 can contact a portion of the interior surface of syringe barrel 14 adjacent open proximal end 19. Accordingly, once backstop 10 is fully fitted to the syringe barrel 14, ridge element 56 contacts the interior surface of syringe barrel 14 (or, as noted, intersection 21 between open proximal end 19 and rim element 22), so as to enhance locking retention of backstop 10 to the syringe barrel 14. Moreover, owing to the smaller diameter aperture 32 vis-à-vis inside diameter "M" of syringe barrel 14, stopper 20 (or, as previously mentioned, stiffening plate 16c of plunger rod 16) is prevented from inadvertent withdrawal from syringe barrel 14, assisted in this case by engagement with the inwardly-facing edge of ridge element 56 if withdrawal is attempted. Note that by providing frusto-conical wall 52 about the periphery of aperture 32, a user may insert either stopper 20 or plunger rod 16 into syringe barrel 14 even if backstop 10 is in place about syringe barrel 14, if such action is desired. However, ridge element 56 may contact stopper 20 or stiffening plate 16c to block any attempt to withdraw the stopper or the plunger rod from the syringe.

Figure 3D:
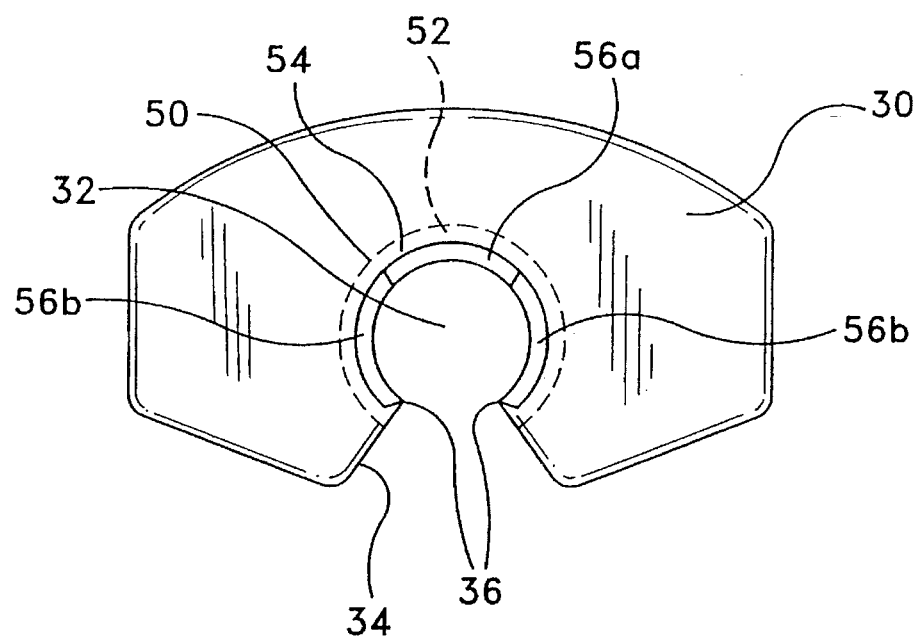
FIGS. 3d and 3e illustrate formation of the ridge element with a variable height.
Figure 3E:
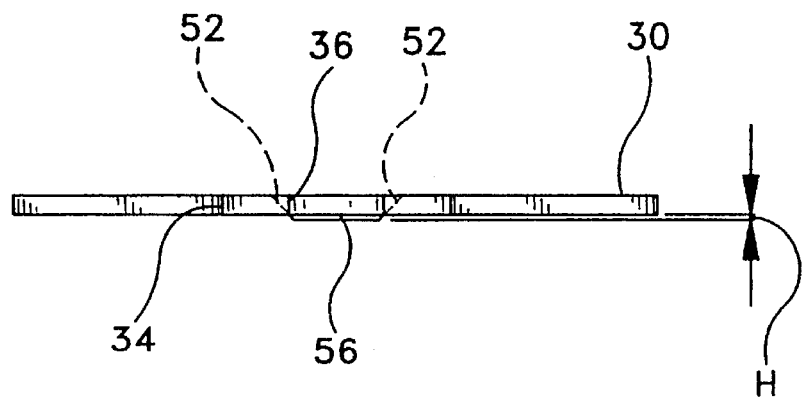

If backstop 10 is configured with ridge element 56 as herein described, to effect easy introduction of backstop 10 over rim 22 and/or open proximal end 19, it will be noted (referring to FIG. 3d) that the height of ridge element 56 may be formed such that a transitional area 56b is provided adjacent each of transition points 36 linking aperture 32 with opening 34. Thus, the height "H" (see FIG. 3e) of ridge element 56 may be configured from virtually zero at transitional points 36, increasing to a portion of maximal, constant height 56a directly opposite opening 34. Accordingly, when maximal portion 56a of ridge element 56 contacts open proximal end 19 of syringe barrel 14, additional force by a user placing backstop 10 over syringe barrel 14 causes maximal portion 56a to be thrust into contact with the interior surface of syringe barrel 14 adjacent open proximal end 19, thereby providing added retention of backstop 10 relative to syringe 14 as previously described.

Figure 6:
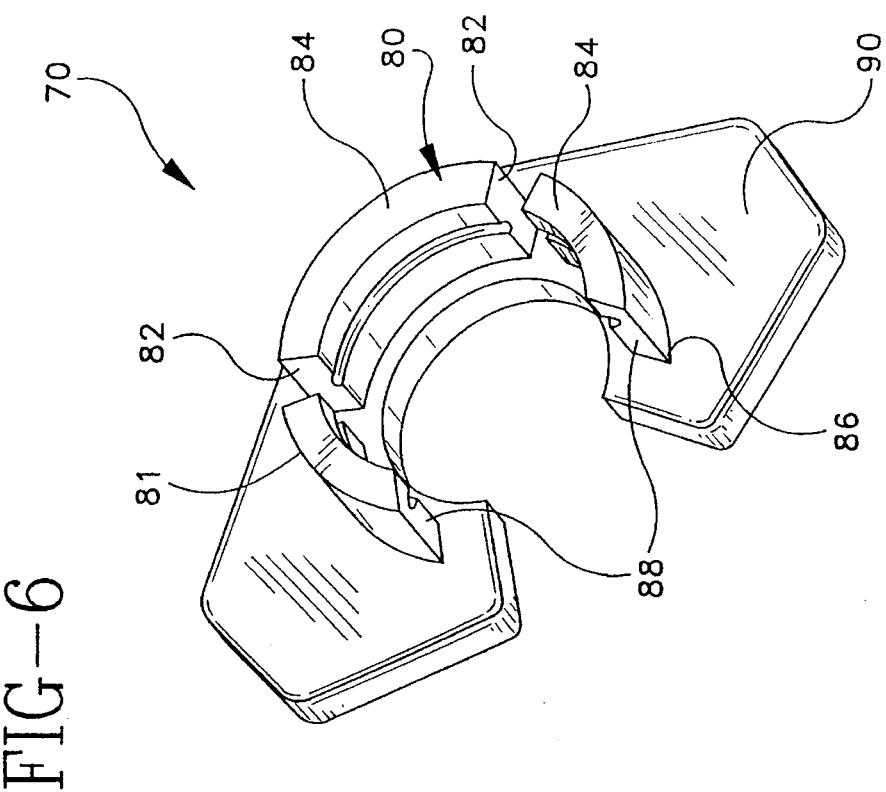
FIG. 6 depicts in bottom view a modification of the backstop device illustrated in FIG. 2.
Figure 5:
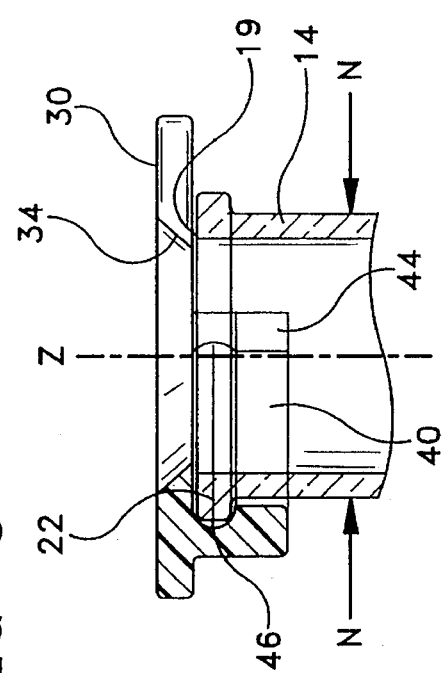
FIG. 5 is a second cut-away view of the embodiment illustrated in FIG. 2, as seen along line 5—5 of FIG. 3.
Figure 7:
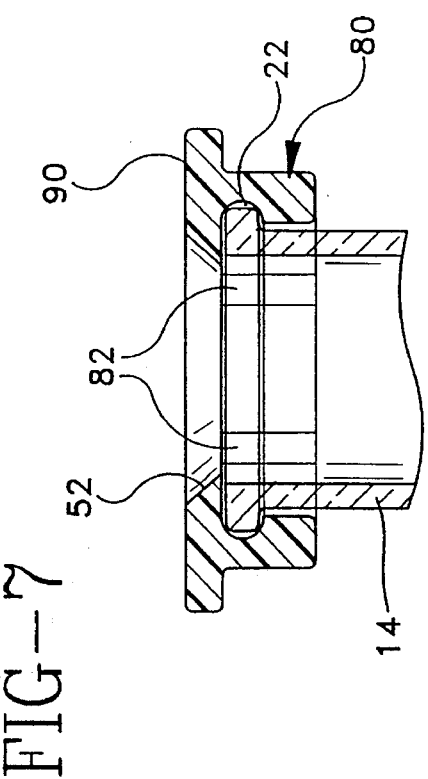
FIG. 7 is a cut-away view of the embodiment depicted in FIG. 6, as mounted to a syringe.

FIGS. 6 and 7 depict an alternate backstop 70 in accordance with the present invention. Here, retaining wall 80 is formed from a plurality of discontinuous sections 84 in a circumferential manner as previously described. As before, a finger plate 90 is disposed adjacent proximal end 86 of each of the discontinuous portions 84. Discontinuous portions 84 define channels 82. By this configuration, retaining wall 80 may be imparted with greater resiliency, allowing opening 88 to expand about the outside diameter of syringe barrel 14. Alternatively, channels 82 may provide openings accommodating various protrusions or the like (not illustrated) found on syringe barrel 14, or perhaps serving as openings allowing the introduction of adhesive materials or the like to secure backstop device 70 to syringe barrel 14.

The backstop in accordance with the present invention may be accommodated to a variety of flangeless syringes. For instance, as illustrated in FIG. 8a, for a flangeless syringe 114 featuring a groove 123 formed adjacent open proximal end 119, backstop 100, and in particular finger plate 130, may be provided with an extension 132 particularly adapted for mating with groove 123 of syringe barrel 114. In FIG. 8b, groove 223 is formed further away from open proximal end 219 of syringe barrel 214. Accordingly, protrusion 232 may be angled downwards so as to mate with the groove. Alternatively, as seen in FIG. 8c, where syringe barrel 314 is provided with a rim element 322, backstop 300, and more particularly finger plate 330, may be provided with an L-shaped, flexible extension 340 having protrusion 342 which, together with a lower surface 344 of finger plate 330, "grasps" rim element 322 therebetween. Finally, referring to FIG. 8d, where syringe barrel 414 features a rim element 422 disposed substantially away from open proximal end 419, finger plate 430 may be provided with a groove 422 formed substantially adjacent distal end 448 of retaining wall 440.

FIGS. 9a–11b depict various alternate methods for affixing the backstop device in accordance with the present invention to the syringe barrel, particularly where reliance is not made on a snap-fit retention between the syringe barrel and the retaining wall. As previously mentioned, the device of the present invention might form a handy, add-on flange for an otherwise flangeless syringe. As depicted in FIGS. 9a–11b, backstop device 500 is configured as an add-on flange component for a flangeless syringe, omitting a top plate in favor of flange rests 501 which will be manipulated by a user. It will be readily apparent to the skilled artisan that the methods referred to herein may be employed for a backstop having a finger plate and associated aperture for preventing inadvertent withdrawal of a stopper or plunger rod from a syringe barrel, as previously described.

Figure 9B:
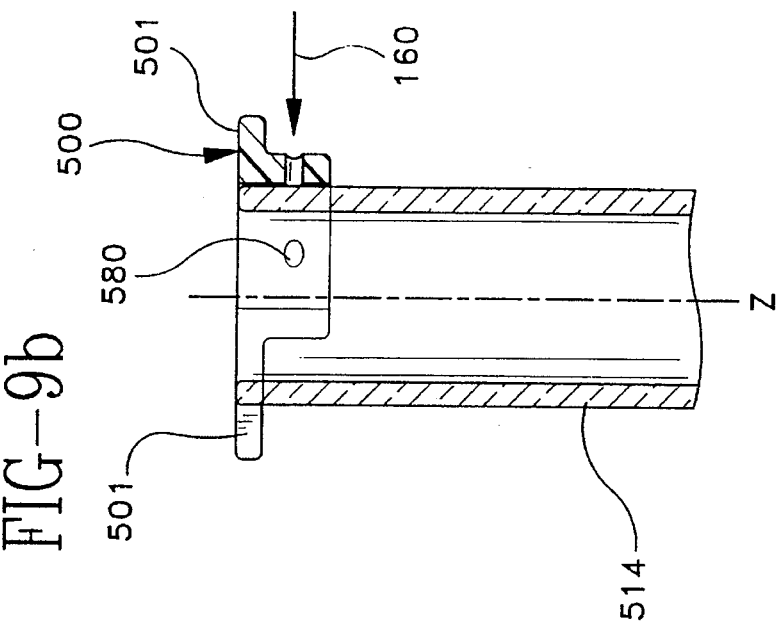
FIGS. 9a through 11b represent various methods for affixing a backstop device in accordance with the present invention to a syringe barrel.
Figure 9A:
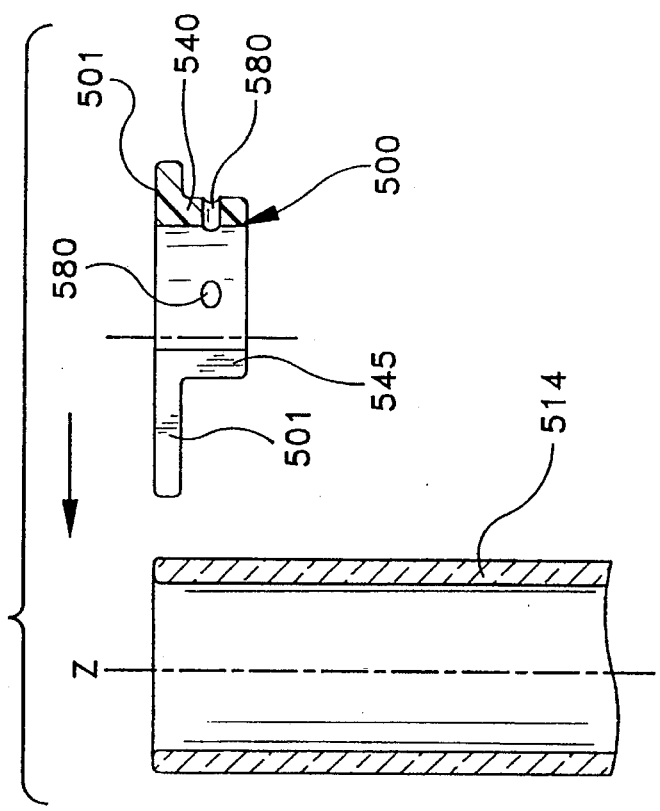
Figure 10B:
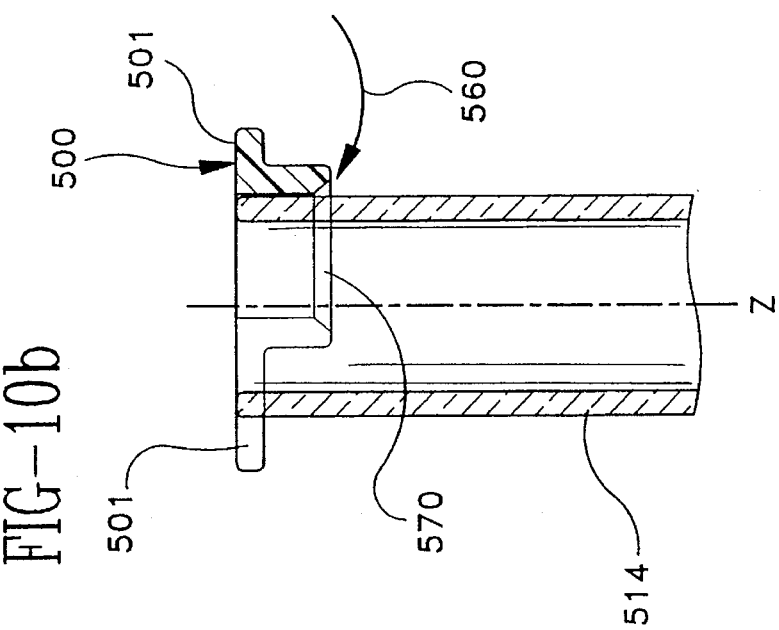
Figure 10A:
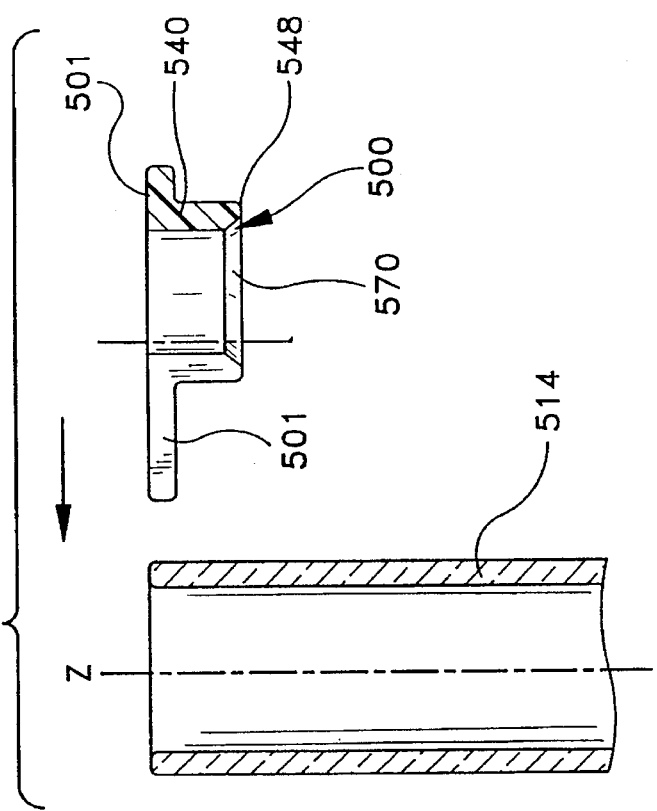
Figure 11B:
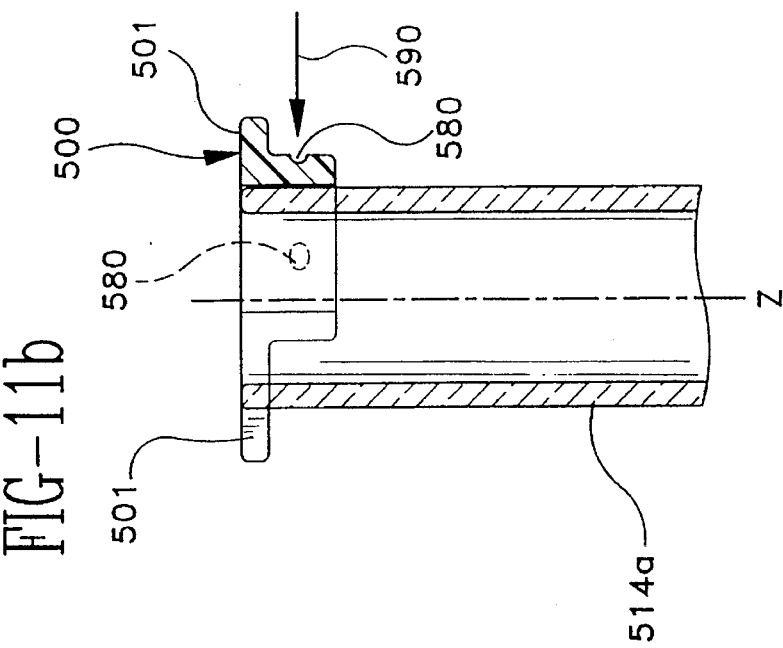
Figure 11A:
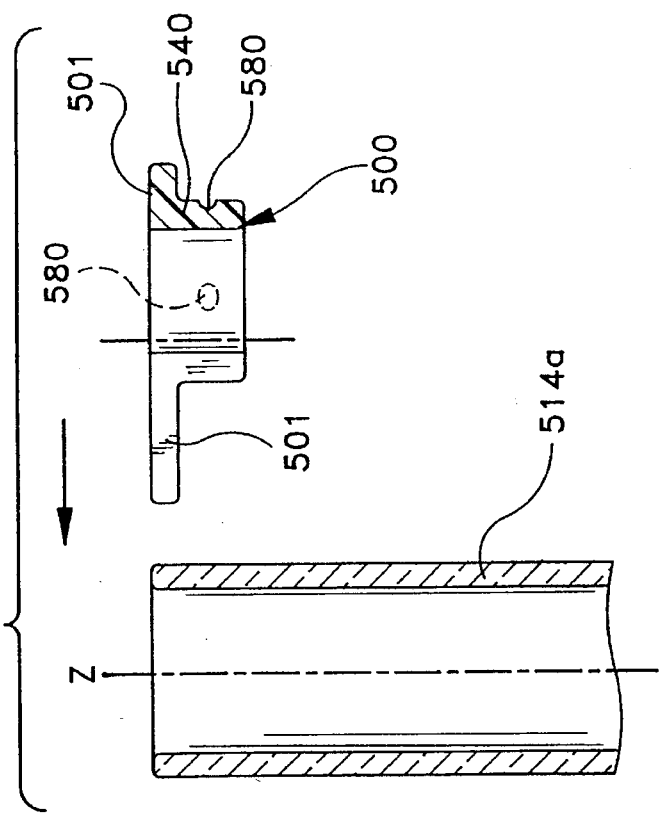

Referring to FIGS. 9a and 9b, for backstop 500 configured for lateral displacement relative to longitudinal axis "Z" of syringe barrel 514, one or more holes 550 may be formed through retaining wall 540. Once backstop 500 is in place relative to syringe barrel 514, adhesive drops 560 may be shot through holes 550 to attach the backstop to the syringe. Alternatively, as seen in FIGS. 10a and 10b, retaining wall 540 can be provided with a chamfered edge 570 adjacent distal end 548. Thus, as backstop 500 is placed relative to syringe 514, adhesive 560 can be injected into chamfered edge 570, adhering the backstop to the syringe. As a further modification, referring to FIGS. 11a and 11b, where syringe 514a is formed from plastic materials, backstop 500 may be similarly configured from a plastic material providing with welding areas 580 disposed about the periphery of retaining wall 540. Welding areas 580 can entail, for instance, depressions in retaining wall 540, such that once backstop 500 is affixed to syringe 514a, appropriate affixation means such as heat sealing devices, ultrasonic devices, laser devices, or the like can act upon those sealing areas 580, sealing and/or welding a plastic backstop 500 to a plastic syringe barrel 514a.

It will be appreciated and understood by those skilled in the art that further and additional forms of the invention may be devised without departing from the spirit and scope of the appended claims, the invention not being limited to the specific embodiments shown.

We claim:

1. A device for preventing inadvertent removal of a stopper from a flangeless syringe, said flangeless syringe having a barrel adapted to retain a plunger rod having a minimum width, said barrel having an outside circumference, and outside diameter, an inside diameter, and an open proximal end, comprising;

a backstop attachable adjacent the open proximal end of said flangeless syringe, said backstop including a retaining wall having proximal and distal ends and defining an opening having a width not greater than the outside diameter of said syringe barrel; and a finger plate affixed to the proximal end of the retaining wall, said finger plate defining an aperture therethrough in communication with the open proximal end of the flangeless syringe, said aperture having a width not greater than the inside diameter of the syringe barrel, and a lead opening communicating with said aperture, said lead opening having a width at least equal to the minimum diameter of the plunger; and a ridge defined about a portion of said aperture, said ridge adapted to engage a portion of said flangeless syringe adjacent the syringe barrel to prevent withdrawal of the stopper from the flangeless syringe.

2. The backstop device of claim 1, wherein said ridge comprises a protrusion formed about a portion of the periphery of said finger plate aperture, said protrusion engageable with the open proximal end of the syringe.

3. The backstop device of claim 2, wherein the protrusion is engageable with an interior portion of the syringe barrel adjacent the open proximal end.

4. The backstop device of claim 1, wherein the width of said finger plate aperture is less than the inside diameter of the syringe barrel, said aperture defining an overhang located over said open proximal end to prevent inadvertent withdrawal of the stopper or the plunger rod from the syringe barrel.

5. The backstop device of claim 4, wherein said finger plate aperture defines a substantially frusto-conically-shaped lead wall oriented towards the open proximal end of the syringe barrel, said lead wall substantially commencing on a top surface of said finger plate and terminating at said overhang.

6. The backstop device of claim 1, wherein a rim element is provided on the outside circumference of said syringe barrel, said retaining wall including a groove adapted to engage therein said rim element.

7. A backstop device for preventing inadvertent removal of a stopper or plunger rod from the open proximal end of a flangeless syringe, said flangeless syringe having a barrel adapted to retain said stopper or plunger rod, said barrel having an outside circumference, an outside diameter, an inside diameter, an open proximal end, and a rim element adjacent the open proximal end, said plunger rod having a minimum width and a maximum width, comprising:

a retaining wall attachable adjacent the open proximal end of the syringe barrel, said a retaining wall adapted to securely engage at least a portion of the outside circumference of the syringe barrel, said retaining wall having proximal and distal ends and an opening having a width not greater than the outside diameter of said syringe barrel, said retaining wall defining a groove for retaining said rim element; and a finger plate affixed to the proximal end of the retaining wall, said finger plate having a top surface and a bottom surface and defining an aperture therethrough in communication with the open proximal end of the flangeless syringe, said aperture having a width not greater than the inside diameter of the syringe barrel, said aperture including a frusto-conical lead wall commencing at the top surface of the finger plate and terminating at the bottom surface of the finger plate, said lead wall defining a diameter at said bottom surface at least equal to the maximum width of the plunger rod, said finger plate defining a lead opening communicating with said aperture, said lead opening having a width at least equal to the minimum diameter of the plunger rod.

8. The backstop device of claim 7, wherein the width of said aperture is less than the inside diameter of the syringe barrel, said finger plate aperture defining an overhang over the open proximal end of the syringe barrel to prevent inadvertent withdrawal of the stopper or the plunger rod from the syringe barrel.

9. The backstop device of claim 7, wherein said retaining wall is formed of one or more discontinuous portions.

* * * * *